United States Patent
Shen

(10) Patent No.: US 9,180,026 B2
(45) Date of Patent: Nov. 10, 2015

(54) ADJUSTMENT-FREE CUSHIONING AIR CYLINDER

(71) Applicants: PRO LIMB International Corp., Shulin (TW); medi GmbH & Co., KG, Bayreuth (DE)

(72) Inventor: Hsin-Fa Shen, Banqiao (TW)

(73) Assignees: PRO LIMB INTERNATIONAL CORP., Shulin (TW); MEDI GMBH & CO. KG, Bayreuth (DE)

( * ) Notice: Subject to any disclaimer, the term of this patent is extended or adjusted under 35 U.S.C. 154(b) by 138 days.

(21) Appl. No.: 13/845,790

(22) Filed: Mar. 18, 2013

(65) Prior Publication Data

US 2013/0264157 A1   Oct. 10, 2013

(30) Foreign Application Priority Data

Apr. 5, 2012   (TW) .............................. 101112028 A

(51) Int. Cl.
| | |
|---|---|
| *A61F 2/50* | (2006.01) |
| *A61F 2/68* | (2006.01) |
| *F16F 9/516* | (2006.01) |
| *A61F 2/74* | (2006.01) |

(52) U.S. Cl.
CPC ................. *A61F 2/68* (2013.01); *F16F 9/5165* (2013.01); *A61F 2002/5006* (2013.01); *A61F 2002/5033* (2013.01); *A61F 2002/6818* (2013.01); *A61F 2002/747* (2013.01); *A61F 2002/748* (2013.01)

(58) Field of Classification Search
CPC ................ A16F 2002/5003; A16F 2002/5033; A16F 2002/6818; A16F 2002/74
USPC ........ 188/268, 282.1, 282.7, 282.8, 270, 301; 267/120, 64.11, 64.13; 623/26, 44
See application file for complete search history.

(56) References Cited

U.S. PATENT DOCUMENTS

| | | | | |
|---|---|---|---|---|
| RE16,582 E | * | 4/1927 | Morinelli | ....................... 188/317 |
| 2,574,314 A | * | 11/1951 | Arden | .............................. 251/51 |
| 3,584,331 A | * | 6/1971 | D'Hooge | ........................... 16/82 |

(Continued)

FOREIGN PATENT DOCUMENTS

| | | |
|---|---|---|
| CN | 1125976 A | 7/1996 |
| DE | 20 2009 016 261 U1 | 3/2010 |
| FR | 2 770 772 A1 | 5/1999 |

*Primary Examiner* — Thomas Irvin
(74) *Attorney, Agent, or Firm* — Lucas & Mercanti, LLP; Klaus P. Stoffel

(57) ABSTRACT

An adjustment-free cushioning air cylinder includes an air cylinder body, a piston, a first check valve, an upper air way, a second check valve and a lower air way. An air chamber is formed inside the air cylinder body. The piston slides in the air chamber. One end of the piston extends to the external of the air cylinder body. The piston does a reciprocating movement in the air chamber and divides the air chamber into an upper air chamber and a lower air chamber. The first check valve is disposed in the piston, one end of the first check valve is connected to the upper air chamber, and the other end is connected to the lower air chamber. The upper air way connects the upper air chamber with the outside. The adjustment-free cushioning air cylinder of the invention does not need to adjust the entering flow rate of the air, but the entering flow rate can be automatically adjusted to produce cushioning resistance as the user is walking according to the walking speed. The present invention has a simple structure, high cushioning performance, lower cost, and is not easy to damage, thus can greatly improve the product competitiveness.

3 Claims, 6 Drawing Sheets

(56) References Cited

U.S. PATENT DOCUMENTS

| | | | |
|---|---|---|---|
| 4,500,075 A * | 2/1985 | Tsuchiya et al. | 267/226 |
| 4,693,454 A * | 9/1987 | Tsuchiya et al. | 267/226 |
| 5,062,857 A | 11/1991 | Berringer | |
| 5,545,233 A | 8/1996 | Fitzlaff | |
| 5,728,174 A * | 3/1998 | Fitzlaff | 623/46 |
| 5,779,735 A * | 7/1998 | Molino | 623/44 |
| 2007/0208431 A1 | 9/2007 | Bisinger | |

* cited by examiner

ADJUSTMENT-FREE CUSHIONING AIR CYLINDER

CROSS REFERENCE TO RELATED APPLICATION

This Application claims the priority of TW Patent Application No. 101112028 filed on Apr. 5, 2012, which application is incorporated herein by reference in its entirety.

TECHNICAL FIELD

The present invention relates to a cushioning air cylinder, especially to an adjustment-free cushioning air cylinder which can be used in a prosthesis joint.

BACKGROUND ART

The air cylinder is a structure which controls air pressure by using the piston's stretch out and draw back and has characteristics of accepting accumulation of pressures and automatically returning after removing external forces due to the compressibility of air pressure. Thus, it is applicable in a lot of living goods such as trunk of the car, automatic door closer, and sports equipment, and apparently an extremely broad range of applications in the market.

The air cylinder is also applied to prosthesis joint and used as medical device providing cushioning function as an alternative of joint. In the common design of the prosthesis joint, the functional purpose is realized mainly by filling the cylinder with air having a predetermined pressure and then cooperating with the operation of the piston rod.

The air needs to be filled and adjusted to reach particular pressure value before the assembly, while after a period of use, the air pressure in the air cylinder body will be gradually leaked, which further leads to lack of air resistance and the defect that the cushioning effect is reduced.

On the other hand, in order to guide the circulation of the internal air, the air cylinder requires additional air flow channel structure, which increases the production complexity and the weight of air cylinder.

In conclusion, the traditional cushioning air cylinder seals the air in the inner of the cylinder body to circulate, which usually requires complex mechanism to reduce the leaking speed of the air; however the defect of air leakage under long-term use has not been overcome yet, the users still have to endure the trouble of repairing and readjustment, and are unable to feel substantial convenience and adequacy.

SUMMARY OF THE INVENTION

The present invention provides an adjustment-free cushioning air cylinder which can be used in prosthesis joint to make the prosthesis have the same cushioning and supporting functions as the body joints.

Based on the above-described contents, the present invention provides an adjustment-free cushioning air cylinder comprising an air cylinder body, a piston, a first check valve, an upper air way, a second check valve and a lower air way. An air chamber is formed inside the air cylinder body, one end of the piston is slidably disposed in the air chamber, and the other end of the piston extends to the external of the air cylinder body. The piston divides the air chamber into an upper air chamber and a lower air chamber and does a reciprocating movement between a first position and a second position in the air chamber. The first check valve is disposed in the piston, one end of the first check valve is connected to the upper air chamber, and the other end is connected to the lower air chamber, so as to allow the air unidirectionally (in one-way) flowing from the upper air chamber to the lower air chamber. An upper air way is formed within the air cylinder body, and connects the upper air chamber with the outside. The second check valve is disposed in the upper air way, one end of the second check valve is connected to the outside, and the other end is connected to the upper air chamber, so as to allow the air unidirectionally (in one-way) flowing from the outside to the upper air chamber. A lower air way is formed in the air cylinder body and connects the lower air chamber with the outside.

Wherein, a bore diameter of the upper air way is larger than that of the lower air way so that the entering flow rate of the air chamber is larger than the discharging flow rate.

The present invention is beneficial in that the adjustment-free cushioning air cylinder uses a design of a simple air way which allows air entering from the top and discharging from the bottom to avoid the complex design of the air way of the traditional cushioning air cylinder. By using the check valve, the present invention can prevent the air from counter-flowing in the air way so that the air cylinder can be automatically and unidirectionally filled with external air, and can avoid the defect of leakage existed in the traditional air cylinder due to the aging of the device. The adjustment-free cushioning air cylinder of the invention does not need to adjust the entering flow rate of the air, but the entering flow rate can be automatically adjusted to produce cushioning resistance as the user is walking according to the walking speed. The adjustment-free cushioning air cylinder of the invention can be directly installed on the prosthesis joint for operation, which avoids the complex adjustment procedure of the traditional air cylinder. The present invention has a simple structure, high cushioning performance, lower cost, and is not easy to damage, thus can greatly improve the product competitiveness.

The features and the technical contents of the present creation will be further appreciated from the following detailed description and figures which are illustrated for reference and explanation only but not to limit the extent of the scope of the present creation.

LIST OF REFERENCE NUMERALS

| | |
|---|---|
| the air cylinder body | 1 |
| the air chamber | 11 |
| the upper air chamber | 111 |
| the lower air chamber | 112 |
| the upper air way | 12 |
| the lower air way | 13 |
| the piston | 2 |
| the upper air way | 21 |
| the first check valve | 3 |
| the second check valve | 4 |
| the sealing ring | 5 |

| | |
|---|---|
| the sound-absorbing cotton | 6 |
| the air adjusting valve | 7 |
| the third check valve | 8 |

The present invention provides an adjustment-free cushioning air cylinder which can be used in prosthesis joint to make the prosthesis to have the same cushioning and supporting functions as the body joints.

Embodiment 1

Figure 1:
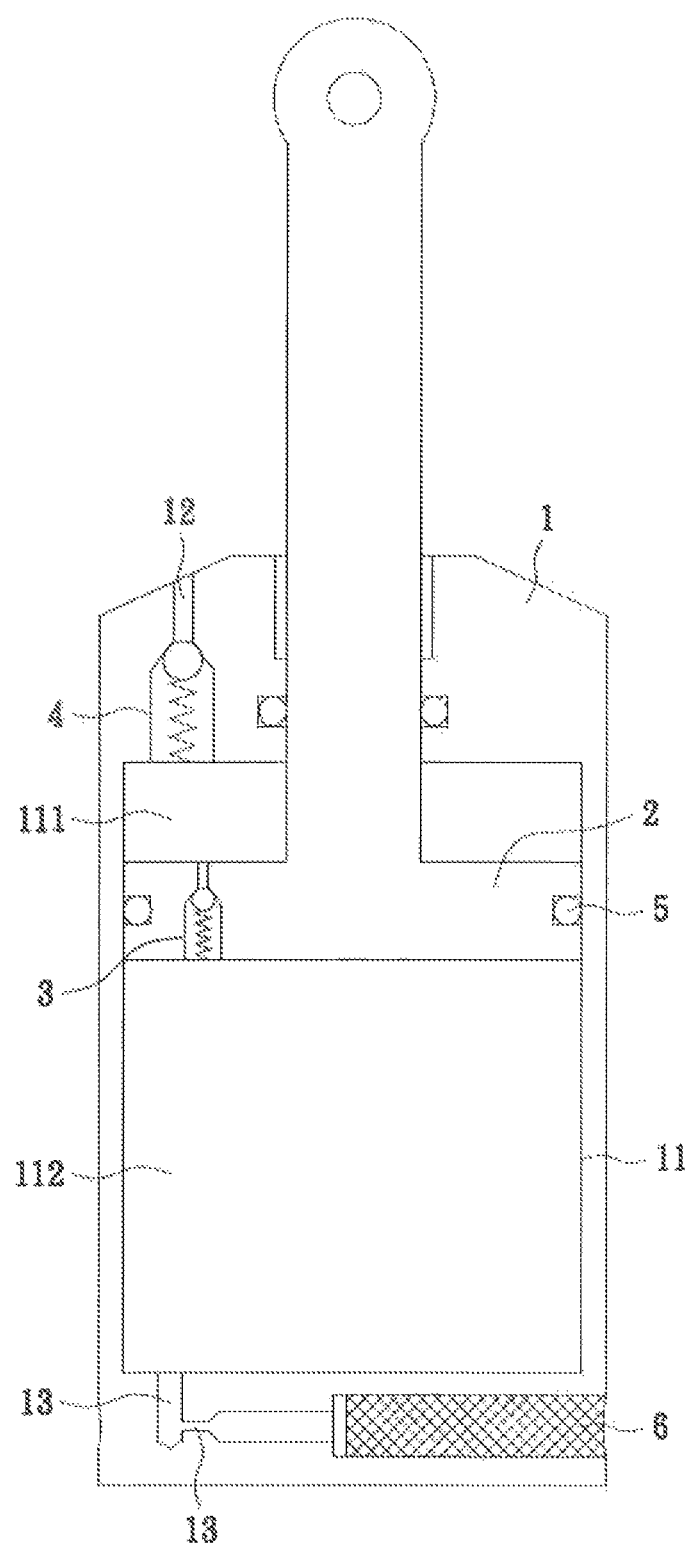
FIG. 1 is a cross-section schematic diagram of the first embodiment of the present invention.

Referring to FIG. 1, the adjustment-free cushioning air cylinder of the present invention comprises an air cylinder body 1, a piston 2, a first check valve 3, an upper air way 12, a second check valve 4 and a lower air way 13.

An air chamber 11 is formed inside the air cylinder body 1, and the air chamber 11 accommodates the piston 2 therein.

The piston 2 extends towards the external of the air cylinder body 1. One end of the piston 2 is slidably disposed in the air chamber 11, and the other end of the piston 2 extends to the external of the air cylinder body 1. A sealing ring 5 is disposed on the piston 2 to close the gap between the piston 2 and the air cylinder body 1, then the air chamber 11 is divided into an upper air chamber 111 and a lower air chamber 112, and the piston 2 optionally does a reciprocating movement in the air chamber 11 so that volumes of the upper air chamber 111 and of the lower air chamber 112 are variable.

The first check valve 3 is disposed in the piston 2, one end of the first check valve 3 is connected to the upper air chamber 111, and the other end of the first check valve 3 is connected to the lower air chamber 112. The air in the upper air chamber 111 can enter the lower air chamber 112 through the first check valve 3, but the air in the lower air chamber 112 can not counter-flow into the upper air chamber 111 due to the stopping function of the first check valve 3.

The air cylinder body 1 forms an upper air way 12 and a lower air way 13, the two ends of the upper air way 12 are connected to the outside and to the upper air chamber 111, respectively, and the two ends of the lower air way 13 are connected to the lower air chamber 112 and to the outside, respectively. Wherein the terminal end of the lower airway is provided with sound-absorbing cotton 6 for eliminating the noise generated when the air is discharged.

Figure 1A:
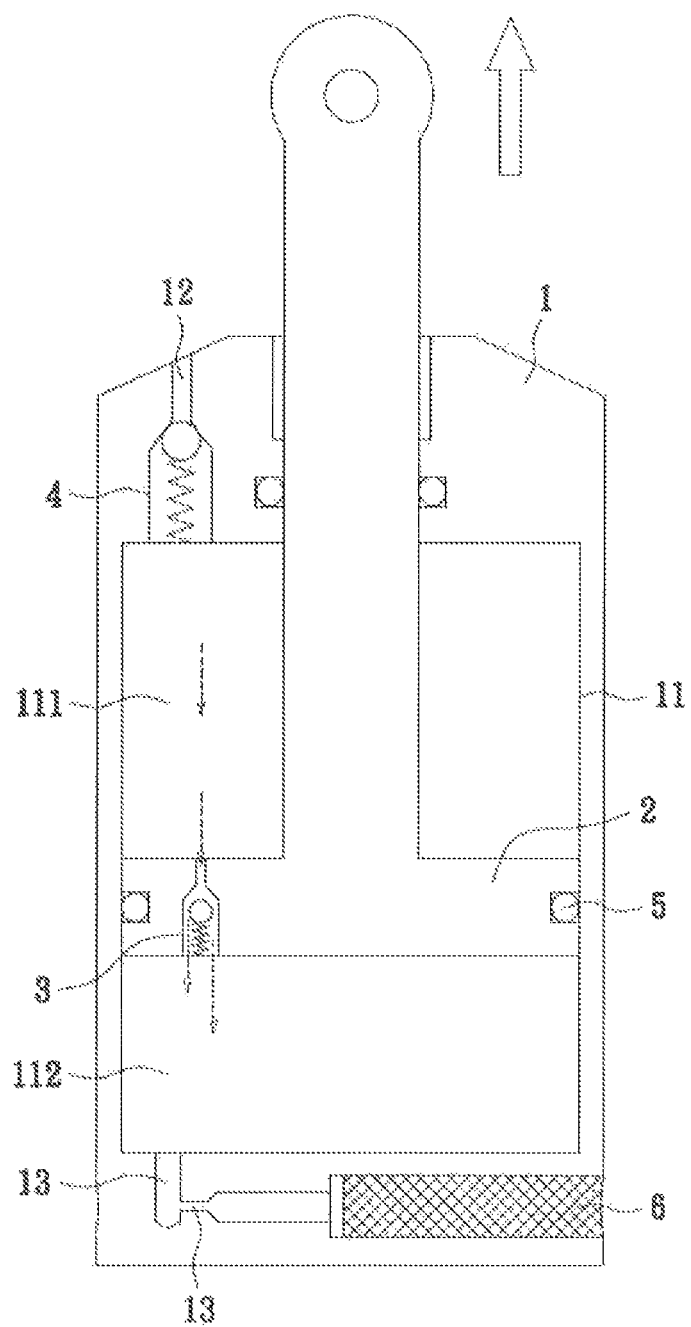
FIG. 1A is a schematic diagram of the air flow direction when the piston is moving upwards of the first embodiment of the present invention.

The second check valve 4 is disposed in the upper air way 12, and can make the air flow unidirectionally (in one-way) from the outside to the upper air chamber 111. As shown in FIG. 1A, when the piston 2 moves upwards, the volume of the upper air chamber 111 is gradually decreased and the air pressure thereof is gradually increased, then the second check valve 4 is closed so that the external air can not enter the upper air chamber 111. Meanwhile the volume of the lower air chamber 112 is gradually increased and the air pressure thereof is gradually decreased, then the first check valve 3 is subjected to a pressure difference and opened so as to fill the lower air chamber 112 with the air from the upper air chamber 111.

Figure 1B:
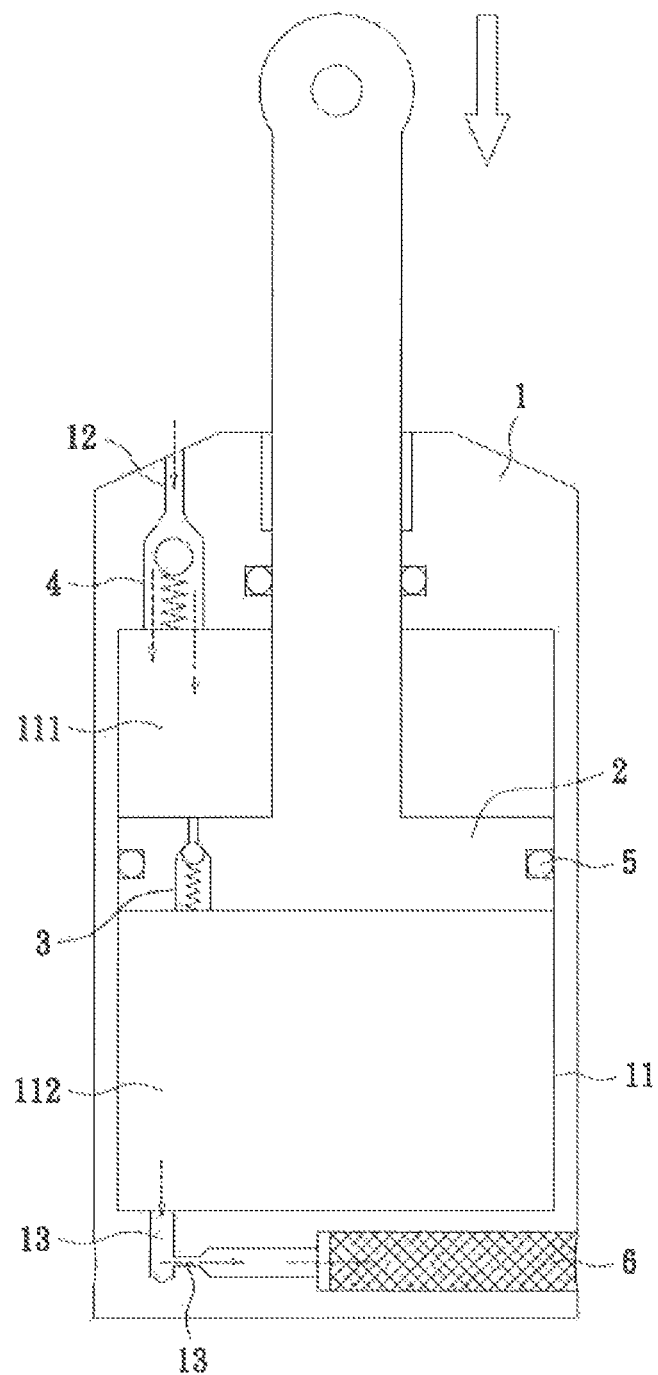
FIG. 1B is a schematic diagram of the air flow direction when the piston is moving downwards of the first embodiment of the present invention.

As shown in FIG. 1B, when the piston 2 moves downwards, the volume of the upper air chamber 111 is increased and the air pressure thereof is gradually decreased, then the second check valve 4 is opened so that the external air can flow into the upper air chamber 111 through the second check valve 4. Meanwhile the volume of the lower air chamber 112 is decreased and the air pressure thereof is gradually increased, then the first check valve 3 is closed so that the air in the lower air chamber 112 can be compressed by the piston 2, flow into the lower air way 13 and discharged out of the air cylinder body 1.

Since the adjustment-free cushioning air cylinder is subjected to a downward-pushing for a longer time than that of upward-pulling, the piston 2 is liable to be in a lower position so that the downward stroke thereof is smaller than the upward stroke. In order to quickly pull up the piston 2, in the present embodiment, a bore diameter of the upper air way 12 is larger than that of the lower air way 13, and a bore diameter of the first check valve 3 is larger than that of the lower upper air way 13, to allow the flow rate for inhaling the air form the external into the air chamber 11 greater than the flow rate for discharging the air out of the air chamber 11. When the piston 2 moves upwards, the first check valve 3 is opened, the air quickly moves to the lower air chamber 112 from the upper air chamber 111, which makes the piston 2 quickly move upwards. When the piston 2 moves downwards, the lower air chamber 112 slowly discharges the air due to the narrower bore diameter of the lower upper air way 13, which makes the lower air chamber 112 have an instantaneous high pressure so that the cushioning function can be realized by means of the air. Moreover, the upward movement speed or the downward movement speed of the piston 2 can determine the air pressure. When the piston 2 moves upwards or downwards slowly, the air in the lower air chamber 112 has enough time to be vented to the external of the air cylinder body 1 through the lower air way 13 and thus the air pressure of the lower air chamber 112 will not be increased; as the upward movement speed or the downward movement speed of the piston 2 is accelerated, since the bore diameter of the upper air way 12 is greater than that of the lower air way 13, the air in the upper air chamber 111 is continuously compressed into the lower air chamber 112 through the first check valve 3, which makes the air in the lower air chamber 112 fail to be discharged timely so that the air pressure of the lower air chamber 112 will be increased. When the upward movement speed or the downward movement speed of the piston 2 is continuously accelerated, the air pressure of the lower air chamber 112 as well as the cushioning resistance will also be increased, so that the effect of automatically adjusting the cushioning resistance with manual-free adjustment can be realized by means of the upward movement speed or the downward movement speed.

Embodiment 2

Figure 2:
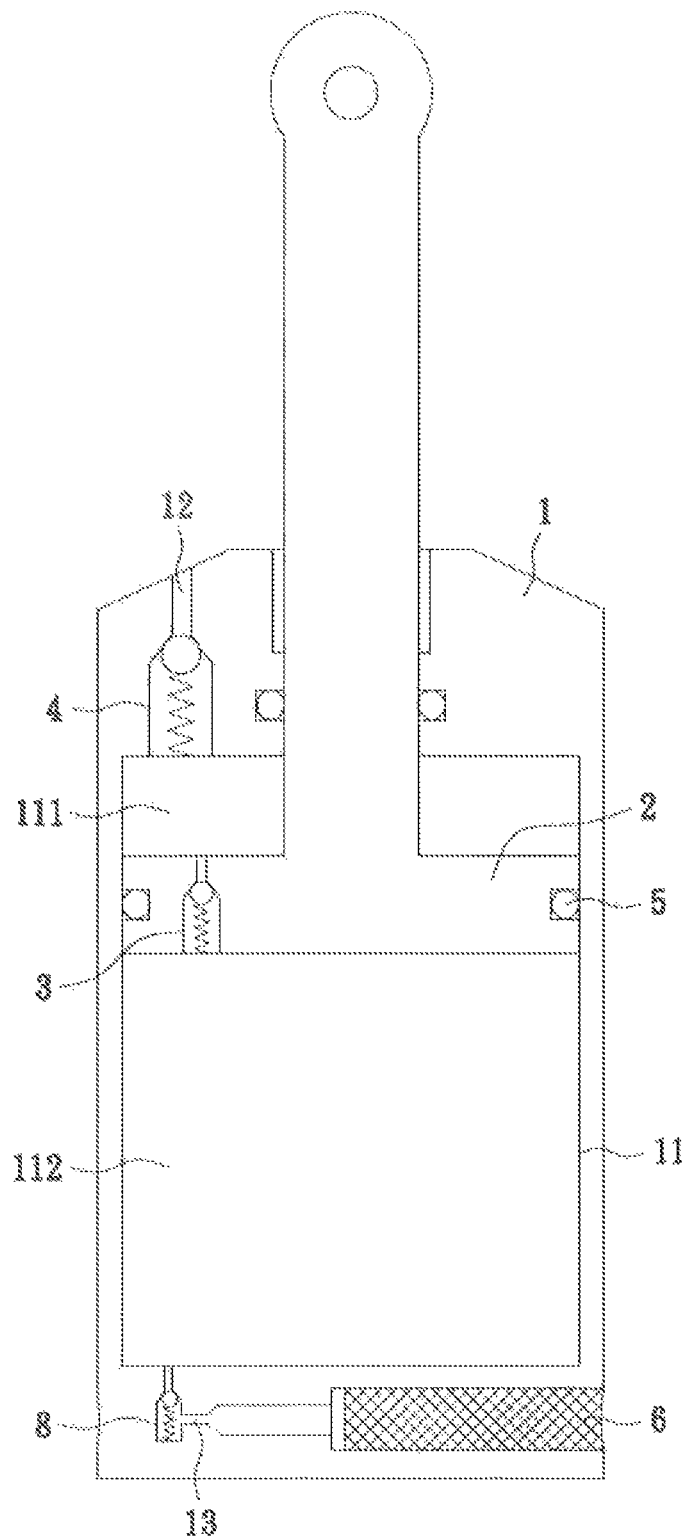
FIG. 2 is a cross-section schematic diagram of the second embodiment of the present invention.

As shown in FIG. 2, the present embodiment is different form the first embodiment in that the present embodiment further includes a third check valve 8 which is disposed in the lower air way 13, the third check valve 8 makes the air flow unidirectionally (in one-way) form the lower air chamber 112 to the outside.

When the piston 2 moves upwards, the air pressure of the upper air chamber 111 is increased and the air pressure of the lower air chamber 112 is gradually decreased, then the first check valve 3 is opened, the second check valve 4 and the third check valve 8 are closed, so that the air chamber 11 is filled with the external air while the air in the air chamber 11 flows into the lower air chamber 112 from the upper air chamber 111 due to the opening of the first check valve 3.

When the piston 2 moves downwards, the air pressure of the upper air chamber 111 is decreased and the air pressure of the lower air chamber 112 is gradually increased, then the first check valve 3 is closed, the second check valve 4 and the third check valve 8 are opened, so that the upper air chamber 111 is filled with the external air entering through the second check valve 4 while the air in the lower air chamber 112 is compressed by the piston 2 to be discharged out of the air cylinder body 1.

By using the design of the first check valve 3, the second check valve 4 and the third check valve 8, the external air can unidirectionally (in one-way) enter the upper air way 12 and be discharged out of the air cylinder body 1 through the lower air way 13. And the diameter bore of the upper air way 12 is larger than that of the lower air way 13, the diameter bore of the first check valve 3 is larger than that of the lower air way 13 so that the adjustment-free cushioning air cylinder fills the air chamber 11 with external air quickly, thus the upward movement speed of the piston 2 is accelerated. Furthermore, since the diameter bore of the lower air way 13 is narrower, the piston 2 pushes down slowly to discharge the air, which makes the lower air chamber 112 have an instantaneous high pressure, so that an effect of cushioning can be obtained by means of the air. When the upward movement speed or the downward movement speed of the piston 2 is accelerated continuously, the air chamber 11 will discharge the air more slowly, the density of the air pressure of the lower air chamber 112 as well as the cushioning resistance will also be increased accordingly, so that the effect of automatically adjusting the cushioning resistance with manual-free adjustment can be realized by means of the upward movement speed or the downward movement speed of the piston 2.

Embodiment 3

Figure 3:
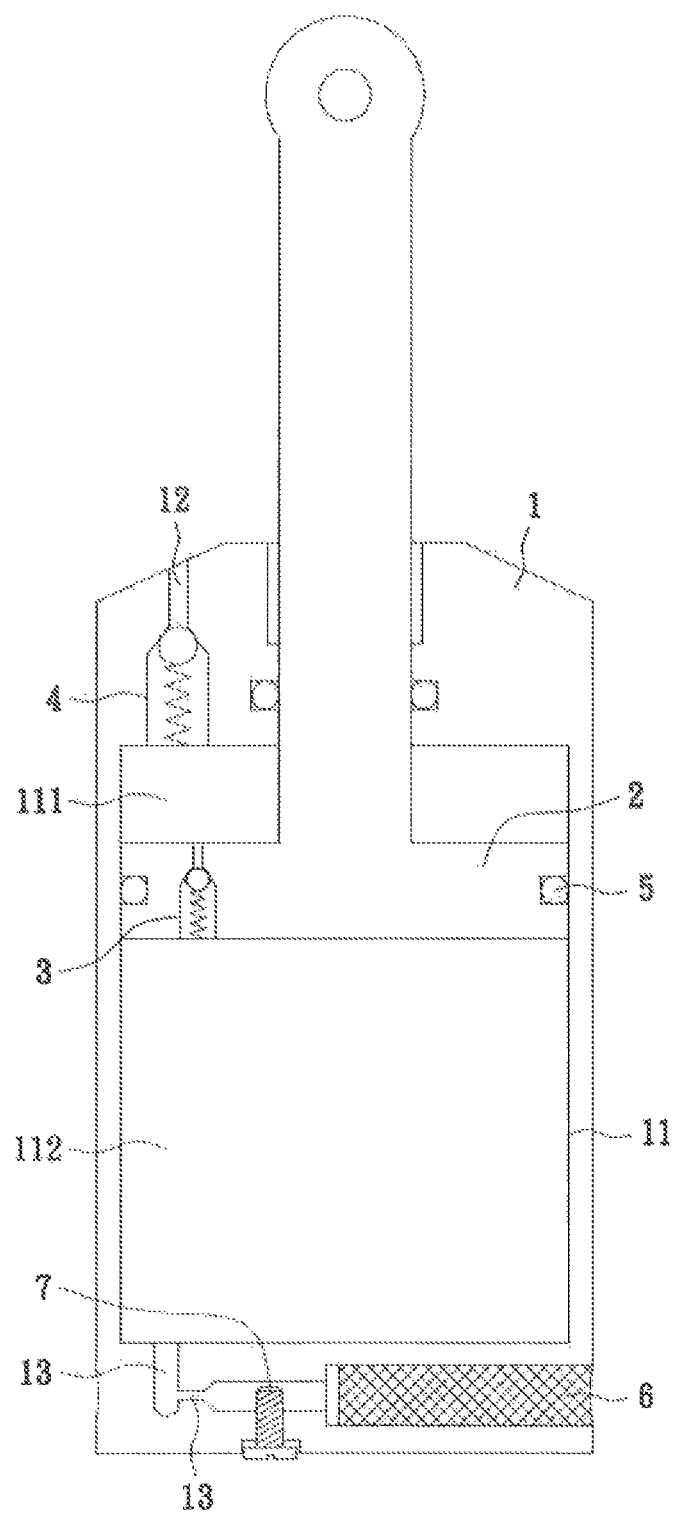
FIG. 3 is a cross-section schematic diagram of the third embodiment of the present invention.

As shown in FIG. 3, the present embodiment is different form the first embodiment mainly in that the present embodiment further includes an air regulating valve 7 disposed in the lower air way 13, by which the air flow rate of the lower air way 13 is selectively set. If the lower air way 13 has a smaller airflow rate, the lower air chamber 112 will have an instantaneous higher pressure, and then the instant downward-pushing stroke of the piston 2 is shortened. The adjustment-free cushioning air cylinder of the present embodiment is suitable for users in a higher speed sport.

It should be noted that the air flow rate of the lower air way 13 is always less than that of the upper air way 12 and of the first check valve 3, no matter how to set the air regulating valve 7, which enables the adjustment-free cushioning air cylinder quickly filling the air chamber 11 with air and slowly discharging the air out of the air chamber 11, so that the cushioning effect can be achieved by means of the air. When the upward movement speed and the downward movement speed of the piston 2 are continuously accelerated, since the air flow rate of the lower air way 13 is always less than that of the upper air way 12 and of the first check valve 3, the air pressure of the lower air chamber 112 and the cushioning resistance will also be increased accordingly, so that the effect of automatically adjusting the cushioning resistance with manual-free adjustment can be realized by the upward movement speed or the downward movement speed of the piston 2. The present embodiment is not limited to the variations of the first embodiment, but also can be combined with the second embodiment to realize the objective of adjusting the air flow rate.

Embodiment 4

Figure 4:
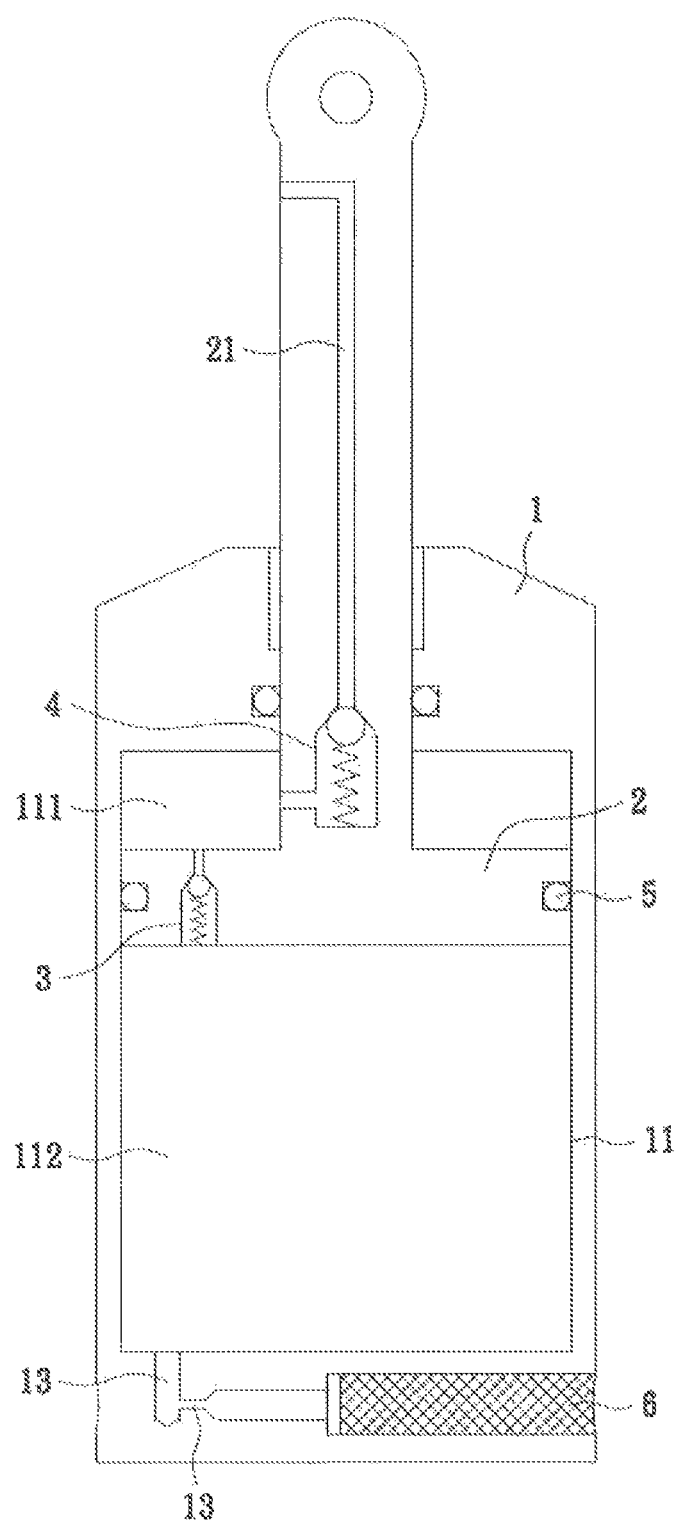
FIG. 4 is a cross-section schematic diagram of the fourth embodiment of the present invention.

As shown in FIG. 4, the present embodiment is different form the first embodiment in that the upper air way 21 is disposed in the piston 2 in the present embodiment, the two ends of the upper air way 21 is connected to the upper air chamber 111 and to the outside, respectively. The present embodiment can further reduce the weight of the piston 2 and thus have an effect of "lightweighting" by forming the upper air way 21 through removing materials from the inner of piston 2.

The present embodiment can also be combined with the second or the third embodiment to reduce the weight of the piston 2.

Potential Effects of the Embodiments

The present invention is beneficial in that the adjustment-free cushioning air cylinder uses a design of a simple air way which allows air entering from the top and discharging from the bottom to avoid the complex design of the air way of the traditional cushioning air cylinder. By using the check valve, the present invention can prevent the air from counter-flowing in the air way so that the air cylinder can be automatically and unidirectionally filled with external air, and can avoid the defect of leakage existing in the traditional air cylinder due to the aging of the device. The adjustment-free cushioning air cylinder of the invention does not need to adjust the entering flow rate of the air, but the entering flow rate can be automatically adjusted to produce cushioning resistance as the user is walking according to the walking speed. The adjustment-free cushioning air cylinder of the invention can be directly installed on the prosthesis joint for operation, which avoids the complex adjustment procedure of the traditional air cylinder. The present invention has a simple structure, high cushioning performance, lower cost, and is not easy to damage, thus can greatly improve the product competitiveness.

It should be stated that, the above description only illustrates the preferred embodiments of the present creation and is not intended to limit the extent of scope thereof. Therefore all the equivalent changes by following the concepts of the specification and the drawings of the present creation should fall within the claimed scope thereof.

What is claimed is:

1. An adjustment-free cushioning air cylinder for use in a prosthesis joint, comprising:
    an air cylinder body, wherein an air chamber is formed in the inner of the air cylinder body;
    a piston, wherein one end of the piston is slidably disposed in the air chamber, and the other end extends to the external of the air cylinder body; the piston divides the air chamber into an upper air chamber and a lower air chamber, and does a reciprocating movement between a first position and a second position in the air chamber;
    a first non-return check valve, wherein the first check valve is disposed in the piston, one end of the first check valve is connected to the upper air chamber, and the other end is connected to the lower air chamber, so as to allow the air unidirectionally flowing from the upper air chamber to the lower air chamber;
    an upper air way, wherein the upper air way is formed within the air cylinder body and connects the upper air chamber with the outside;
    a second non-return check valve, wherein the second check valve is disposed in the upper air way, one end of the second check valve is connected to the outside, and the other end is connected to the upper air chamber so as to allow the air unidirectionally flowing from the outside to the upper air chamber; and
    a lower air way, wherein the lower air way is formed inside the air cylinder body and connects lower air chamber with the outside; and
    a third non-return check valve which is disposed in the lower air way to allow the air unidirectionally flowing from the lower air chamber to the outside;
    wherein a bore diameter of the upper air way is larger than that of the lower air way so that the entering flow rate of the air chamber is larger than the discharging flow rate.

2. The adjustment-free cushioning air cylinder of claim 1, wherein an air regulating valve is disposed in the lower air way to adjust the air flow rate of the lower air way.

3. The adjustment-free cushioning air cylinder of claim 1, wherein a sound-absorbing cotton is disposed at the lower air way.

* * * * *